United States Patent [19]

Samiotes et al.

[11] Patent Number: 4,943,279
[45] Date of Patent: Jul. 24, 1990

[54] MEDICAL PUMP WITH INFUSION CONTROLLED BY A DETACHABLE CODED LABEL

[75] Inventors: Nicholas G. Samiotes, Westwood; Paul Lucas, Groton, both of Mass.

[73] Assignee: C.R. Bard, Inc., Murray Hill, N.J.

[21] Appl. No.: 251,563

[22] Filed: Sep. 30, 1988

[51] Int. Cl.⁵ .............................................. A61M 1/00
[52] U.S. Cl. ........................................ 604/151; 604/67; 604/154; 128/DIG. 13
[58] Field of Search ................. 604/66, 67, 151, 152, 604/153, 154, 155; 128/DIG. 3, DIG. 13; 417/44

[56] References Cited

U.S. PATENT DOCUMENTS

| | | | |
|---|---|---|---|
| 4,105,138 | 8/1978 | Lehmann et al. | 222/14 |
| 4,275,727 | 6/1981 | Koeri-Szanto | 128/214 |
| 4,464,172 | 8/1984 | Lichtenstein | 128/DIG. 13 X |
| 4,529,401 | 7/1985 | Leslie et al. | 604/131 |
| 4,551,134 | 11/1985 | Slavik et al. | 128/DIG. 13 X |
| 4,559,037 | 12/1985 | Franetzki et al. | 604/151 |
| 4,565,542 | 1/1986 | Berg | 604/131 |
| 4,624,661 | 11/1986 | Arimond | 604/151 |
| 4,648,869 | 3/1987 | Bobo, Jr. | 604/49 |
| 4,673,391 | 6/1987 | Kondo et al. | 604/141 |
| 4,690,673 | 9/1987 | Bloomquist | 604/67 |
| 4,714,462 | 12/1987 | DiDomenico | 604/67 |
| 4,722,734 | 2/1988 | Kolin | 604/151 |
| 4,741,732 | 5/1988 | Crankshaw et al. | 604/67 X |
| 4,741,736 | 5/1988 | Brown | 604/134 |
| 4,752,289 | 6/1988 | Balding et al. | 604/118 |
| 4,838,860 | 6/1989 | Groshong et al. | 604/152 |

Primary Examiner—Richard J. Apley
Assistant Examiner—Joe H. Cheng
Attorney, Agent, or Firm—Kane, Dalsimer, Sullivan, Kurucz, Levy, Eisele and Richard

[57] ABSTRACT

This invention relates to a microprocessor-based medical pump with a number of manual controls. The operation of this pump requires the attachment of a magnetic label to the front of the pump. This magnetic label includes a given number of strong permanent magnets in a pre-determined configuration which indicate the pharmaceutical product type and concentration to be infused. The magnetic label also changes the visual scales around the manual controls. Hall Effect sensors read the pre-determined configuration and send the data to the microprocessor which also reads the manual controls. Using the pre-determined configuration data and the manual control data, the microprocessor determines the desired infusion parameters.

16 Claims, 4 Drawing Sheets

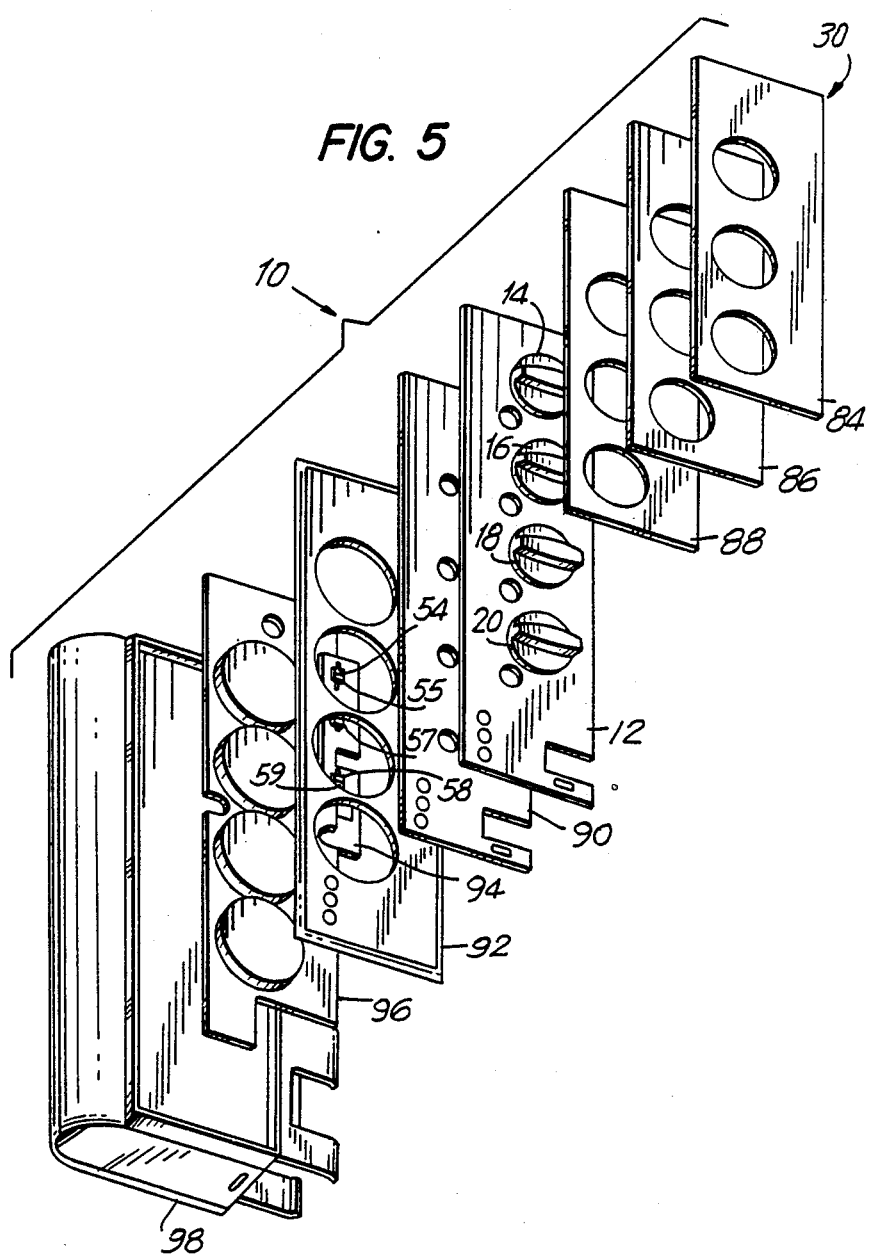

MEDICAL PUMP WITH INFUSION CONTROLLED BY A DETACHABLE CODED LABEL

BACKGROUND OF THE INVENTION

1. Field of Invention

The present invention relates to a medical pump which has its pumping rate and pumping interval controlled by a magnetic label. This label visually alters the scales on the various manual controls, and, via the positions of magnets which are sensed by Hall Effect sensors within the pump, communicates a value to the pump which takes into account various factors relating to the desired pharmaceutical product infusion.

2. Description of the Prior Art

Medical pumps with infusion parameters controlled by manual dial settings, microprocessors, and electrical devices are well-known in the prior art. For example, U.S. Pat. Nos. 3,701,345 and 4,320,757 disclose apparatus with electrical drive systems for injecting controlled amounts of fluid into a patient. However, these references require the user to be cognizant of several variables such as the concentration of the pharmaceutical product within solution, the desired infusion rate of the pharmaceutical product, the weight of the patient, the total amount of pharmaceutical product desired to be injected into the patient either on a total or per unit of weight or mass, and even the cross-sectional area of the plunger of the ampule so as to calculate a desired velocity and total displacement of the plunger within the ampule of the syringe. Moreover, the user would have to be cognizant even of the units of all of these variables so as to not make a calculative error. Any of these calculative errors could be disastrous to the patient.

References which show an injection system with a programmable means responsive to a keyboard include U. S. Pat. Nos. 4,529,401; 4,624,661; 4,681,563; and 4,722,734. However, these systems still require several keystrokes on the part of medical personnel with a wide range of skill levels, some of whom may find such a computer-like device intimidating. Further, the exhaustion and hurried pace of many medical situations are not conducive to the consistently accurate programming needed for such devices. Further, the difficulty in operating these devices is compounded when, after the infusion starts, medical personnel realize that the dose must be adjusted to accommodate the patient's metabolism, tolerance, and sensitivities with respect to the pharmaceutical product being infused.

U.S. Pat. No. 4,741,732 uses a complicated programming scheme to effect generalized infusion rate profiles of a pharmaceutical product so as to maintain a constant pharmaceutical product concentration within the patient. This device may still have the deficiencies listed in the previous paragraph in that a manual entering of all of the data needed for a particular pharmaceutical product concentration, patient body weight, plunger cross section is very error prone for exhausted or hurried medical personnel. These deficiencies are mitigated, only in part, by including an EPROM (electrically programmable read-only memory) which includes instructions and/or data in machine or object language form relating to the general characteristics of the desired time-dependent infusion rate profile. Even when using the EPROM device, this device is complicated and is directed more toward delivering complex time-dependent infusion rate profiles rather than providing a simple, "user-friendly" device with visually verifiable controls, for infusing a given dose of a pharmaceutical product to a patient.

OBJECTS AND SUMMARY OF INVENTION

It is therefore an object of this invention to provide an apparatus for infusing a wide variety of narcotics, muscle relaxants and vasoactive pharmaceutical products into a patient wherein the parameters relating to the infusion are programmed by the user into the device.

It is therefore a further object of this invention that the programming of these infusion parameters is simple and not intimidating.

It is therefore a further object of this invention that the programming of these infusion parameters is easy to verify visually.

It is therefore a further object of this invention that the user is able to vary the infusion rate manually after the initial programming so as to accommodate the patient's metabolism, tolerance, and sensitivities with respect to the pharmaceutical product being infused.

It is therefore a still further object of this invention that the apparatus be adaptable to a broad range of infusion applications.

The control device of the present invention includes three knobs which are related to infusion parameters. The first knob is set according to the desired infusion rate of the pharmaceutical product, the second knob is set according to the body weight of the patient, and the third knob is set according to a bolus, or the total amount of pharmaceutical product desired by unit weight of the patient. A microprocessor uses these variables to calculate a desired infusion flow, velocity of the plunger, total bolus volume, and bolus duration.

A fourth knob is used to set the mode of operation, such as "purge", "off", "stop/confirm", "bolus start" and "infuse". A five-digit liquid crystal display and several light emitting diodes indicate the mode of operation and the total volume infused.

In order for this device to accommodate infusion of various pharmaceutical products of different concentrations, and ranges of infusion rates, a different magnetic label is manufactured for each pharmaceutical product configuration. These labels spell out the pharmaceutical product name and concentration. These labels fit over the front panel of the pump control unit, around the knobs, so as to alter the visual scales of the desired infusion rate, bolus, and possibly patient weight knobs. So that the new pharmaceutical product parameters and altered scales are properly taken into account, magnetic devices are embedded within predetermined sections of the labels. The position and polarity of these devices are related to the aforementioned parameters and scales and are sensed by Hall Effect sensors within the pump control device. A microprocessor within the pump control device uses the positions to which the knobs are set along with the information from the Hall Effect sensors to determine the desired infusion flow, plunger velocity, total bolus volume and bolus duration.

BRIEF DESCRIPTION OF THE DRAWINGS

FIG. 5 is an exploded view of the pump control unit and the magnetic label system.

DETAILED DESCRIPTION OF THE PREFERRED EMBODIMENT

Figure 1:
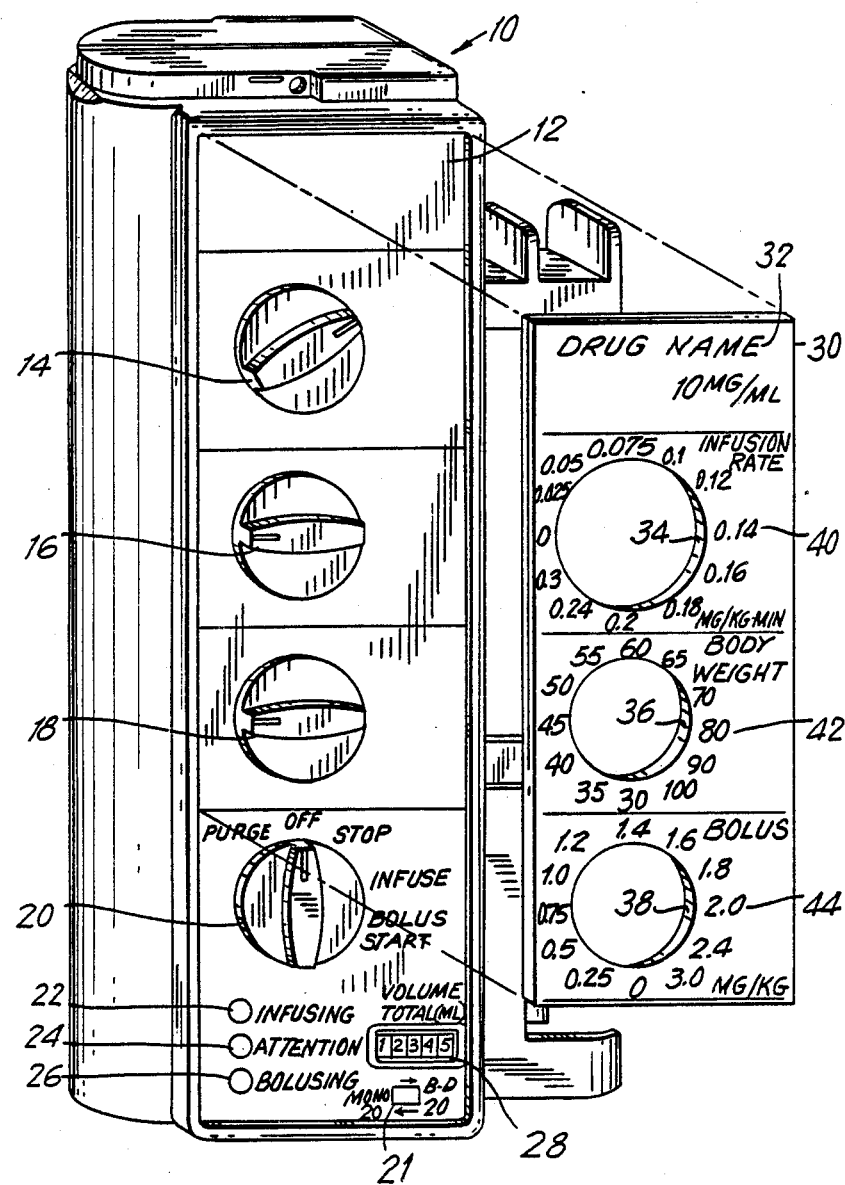
FIG. 1 is a front perspective view of the pump and the magnetic label of present invention.

Referring now to the drawings in detail wherein like numerals indicate like elements throughout the several views, Apparatus 10 is disclosed in FIG. 1. The front plate 12 of apparatus 10 has four knobs—an infusion rate knob 14, a body weight knob 16, a bolus knob 18, and an operational mode selection knob 20.

The operational mode selection knob 20 has "Off", "Purge", "Stop/Confirm", "Infuse", and "Bolus Start" settings.

A two position switch 21 is used to select the syringe type. The preferred embodiment allows only for standard twenty or sixty cubic centimeter (cc) syringes, although those skilled in the art will realize that more positions could be allowed or that scaling factors proportional (or inversely proportional) to the plunger cross section of the syringe could be incorporated into the information encoded into the label 30.

Additionally, the front plate 12 of apparatus 10 includes an "Infusing" light emitting diode 22, an "Attention" light emitting diode 24, a "Bolusing" light emitting diode 26, and a five-digit liquid crystal display 28.

FIG. 1 also shows the magnetic label 30. Magnetic label 30 includes an alphanumeric listing 32 of the pharmaceutical product type and concentration in bold print. Magnetic label 30 also includes three apertures 34, 36, 38 which are outlined, respectively, by scales 40, 42, 44, for infusion rate, body weight and bolus, respectively.

Aperture 34, for the infusion rate knob 14, has scale 40 in units of milligrams of pharmaceutical product per kilogram of patient body weight (or mass) per minute. This may be replaced with milliliters of pharmaceutical product per kilogram of patient body weight per minute, milligrams of pharmaceutical product, or milliliters of pharmaceutical product. The milliliters or milligrams refers to the active pharmaceutical product contained within the solution of the syringe 11 and not to the volume or mass of solution.

Aperture 36, for the patient body weight (or mass) knob 16, has a scale 42 in units of kilograms. As will be described in more detail later, this knob 16 will be active only when the units of infusion rate and bolus are on a per unit patient weight basis.

Aperture 38, for the bolus knob 18, has a scale 44 in units of total milligrams of pharmaceutical product infused per kilogram of patient body weight. This may be replaced with milliliters of pharmaceutical product per kilogram of patient body weight, milligrams of pharmaceutical product, or milliliters of pharmaceutical product. Again, the milliliters or milligrams refers to the active pharmaceutical product contained within the solution of the syringe 11 and not to the volume or mass of solution.

The ranges of these scales 40, 42, and 44 are chosen so as to be appropriate for the pharmaceutical product type and concentration which is specified on alphanumeric listing 32. Further, the units of these scales, particularly infusion rate and bolus (which may be given in units using milliliters or milligrams, and on a total or per patient body weight basis) are chosen in accordance that associated with the particular pharmaceutical product and solution of interest. If the units of infusion rate and bolus are given on a total basis rather than a per unit of patient body weight, then the scale 42 for body weight is labelled "Inactive".

Similarly, for some "Infusing" modes, as opposed to "Bolusing" modes, where either the body weight or bolus scales 42, 44 are unnecessary in that the pharmaceutical product is to be infused at a certain rate for an indefinite time period, these scales are changed to low infusion rate scales, while the infusion rate scale 40 is changed to a high infusion rate scale. As will be described in more detail, the user sets one of the infusion rate scales to zero, and the other to the desired high or low infusion rate.

Front plate 12, or other closely related structural elements of apparatus 10 have ferrous or similar components so that the label 30 can magnetically attach to apparatus 10.

Figure 2:
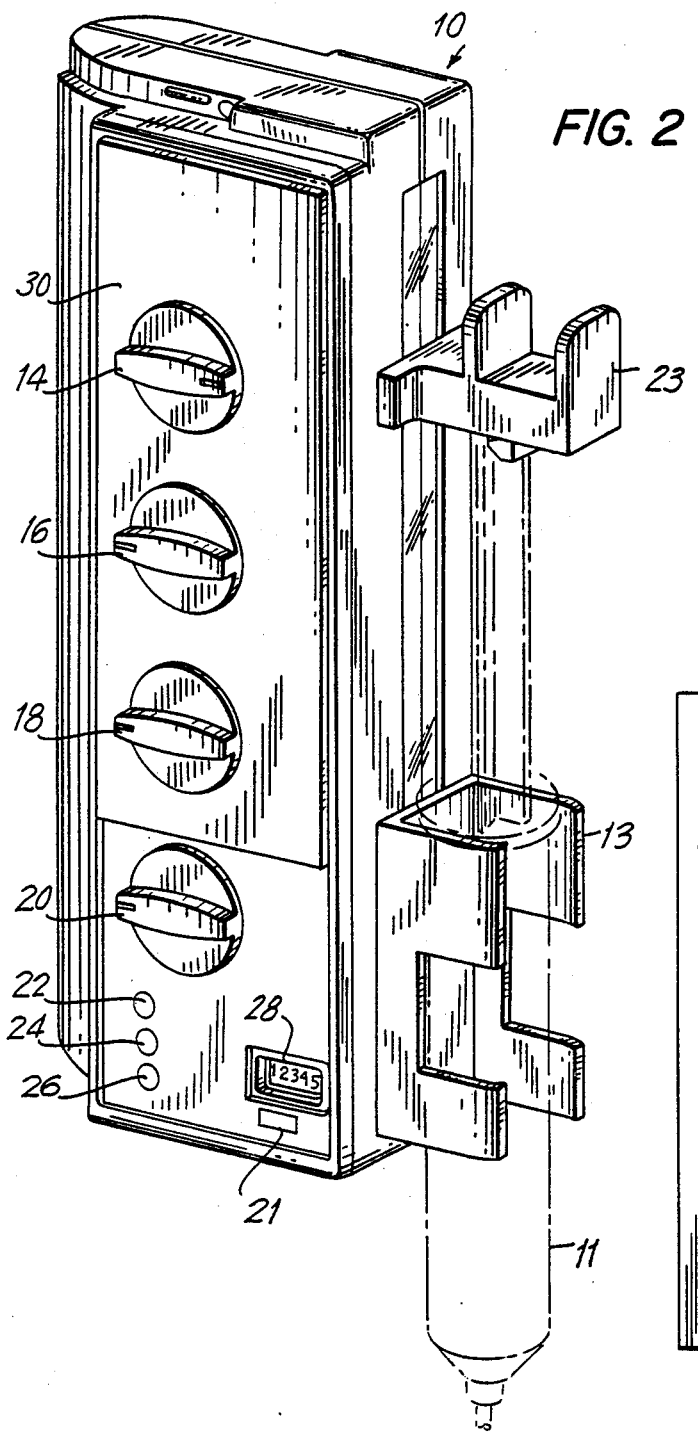
FIG. 2 is a front perspective view of the pump of the present invention, along with an attached syringe shown in phantom.

FIG. 2 discloses the front of apparatus 10 at such an angle to disclose syringe 11 attached to apparatus 10 by clip 13. Plunger driver 23 engages the plunger of syringe 11 and is mechanically driven by drive mechanism 70 (see FIG. 4) to expel the pharmaceutical product. The engagement of this pump apparatus 10 to the syringe 11 and the mechanical details of the drive mechanism 70 are disclosed in commonly assigned application 088,806, filed Aug. 24, 1987 and allowed Sept. 2, 1988, now U.S. Pat. No. 4,804,368. Those skilled in the art will realize that several different methods for engaging syringe 11 are possible without departing from the scope of this invention.

Figure 3:
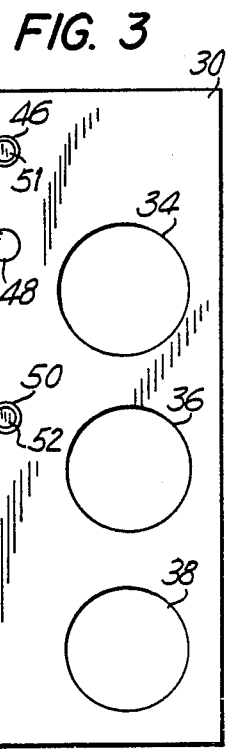
FIG. 3 is a rear plan view showing the magnetic data devices of the magnetic label of the present invention.

Magnetic label 30, in addition to having magnetic properties throughout its structure, also includes apertures 46, 48, and 50 in its rear portion into which strong Samarium Cobalt (rare earth) magnets may be inserted as shown in FIG. 3. FIG. 3 shows magnets 51 and 52 placed into apertures 46 and 50. The position and polarity of magnets 51 and 52 within apertures 46, 48, and 50 are related to the pharmaceutical product concentration (as spelled out by alphanumeric listing 32), the adjustments necessary to compensate for the changes between scales listed on front plate 12 around knobs 14, 16, and 18 and the scales 40, 42, and 44 on magnetic label 30, and any other variables which those skilled in the art may realize are necessary for the proper calculation of desired infusion flow, plunger velocity, total bolus volume and bolus duration.

As previously described, this particular embodiment uses three possible magnet locations (that is apertures 46, 48 and 50), wherein each magnet has one of two possible polarities. Magnets of a single strength within a given tolerance are used. In order to provide a method for verifying the integrity of the label, magnets 51, 52 must be inserted into exactly two of the apertures 46, 48 and 50. Further, the apparatus 10 will not operate unless a label 30 with exactly two magnets 51, 52 are placed upon the apparatus in a position as shown in FIG. 3.

This allows for 12 possible combinations of placement and polarity (a factor of three for choosing two out of three apertures and two factors of two, one for each polarity selection). Those skilled in the art will realize that more locations or levels of magnetic strength are possible in order to allow for more possible combinations without departing from the scope of this invention. Those skilled in the art will also realize that a single combination of magnets will suffice for more than one combination of the aforementioned variables. For instance, all other things being equal, different concentrations of pharmaceutical products could be compensated for by different scales on the magnetic label 30 without changing the configuration of magnets 51, 52 within apertures 46, 48, and 50.

The dimensions of magnetic label 30 and the diameter and spacing of apertures 34, 36 and 38 are chosen so that magnetic label 30 can fit over front plate 12 as shown in FIG. 1, thereby altering the scales which are visually associated with knobs 14, 16, and 18.

Those skilled in the art will realize that other methods of communication from the label 30 to the apparatus 10 are available. These methods include:

1. Pins and Connectors

Pins or connectors could be attached and coded on a PC board to which the label is attached.

2. Optoelectronics

The label could incorporate reflective or transmissive optoelectronics. For example, such a reflective system would have a reflective code on the label. A sensor and emitter combination would be installed in the pump and would be focused on the rear of the label thereby reading the code.

3. Microswitch and Pin

Microswitches could be installed in the pump with through-holes over the switches. Activator pins attached to the label would pass through the holes and activate the switches. Many different variations of switches could be used such as membrane switches, pushbutton switches, etc.

4. Capacitive and Inductive Sensing

Capacitive and inductive sensing would replace magnetic sensing.

Figure 4:
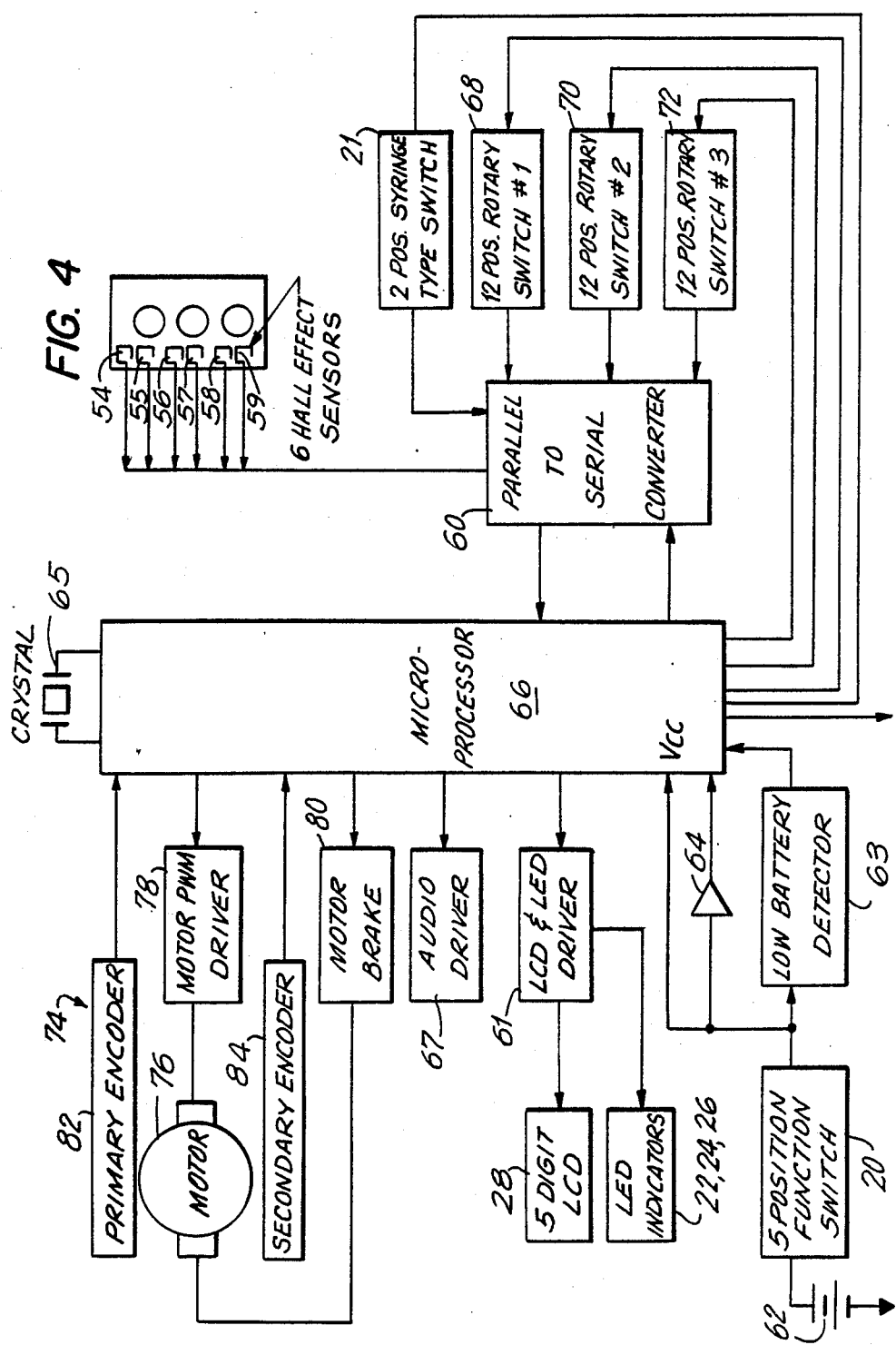
FIG. 4 is a block diagram of the microprocessor-based control system of the present invention.

FIG. 4 discloses a block diagram of the internal electronics of apparatus 10. Hall Effect sensors 54, 55, 56, 57, 58 and 59 are positioned to be on the interior side of front plate 12 adjacent to apertures 46, 48, and 50 when magnetic label 30 is attached to the apparatus as shown in FIG. 1. Each aperture has two sensors associated therewith—one sensor two detect a north polarity and one sensor to detect a south polarity. The Hall Effect sensors 54, 55, 56, 57, 58 and 59 have a current running through them. When the sensors are subjected to a magnetic field normal to the current density vector from magnets 51, 52 placed into apertures 46, 48, and 50, the current through the sensors 54, 55, 56, 57, 58 and 59 changes. This change in current is detected and converted into a digital signal by the sensors 54, 55, 56, 57, 58 and 59. This digital signal is transmitted to a parallel to serial converter 60, which in turn, communicates these values to microprocessor 66.

Microprocessor 66 drives the LCD and LED driver 61, which in turn drives LEDs 22, 24, 26 and LCD 28. Microprocessor 66 also drives audio driver 67 in order to generate audio signals such as "beeps".

Microprocessor 66 is responsive to power supply 62, low battery detector 63, reset control 64 and timing crystal 65 as shown in FIG. 4.

The position of the infusion rate knob 14, the body weight knob 16, and the bolus knob 18 are communicated to microprocessor 66 via rotary switches 68, 70, 72 and the parallel to serial converter 60. The position of operational mode selection knob 20 is communicated to microprocessor 66 in that knob 20 is interposed between power supply 62 and microprocessor 66. The microprocessor 66 calculates the desired infusion as a product of the factors below:

1. The infusion rate as indicated by the position of infusion rate knob 14.
2. The patient body weight as indicated by the position of body weight knob 16.
3. A scaling factor to convert the position of the infusion rate knob 14 to the infusion rate indicated on scale 40 of the magnetic label 30.
4. A scaling factor to convert the position of the patient body weight knob 16 to the patient body weight indicated on scale 42 of the magnetic label 30.
5. The inverse of the pharmaceutical product concentration indicated by alphanumeric listing 32 on magnetic label 30.

Applications where the infusion rate is given on an absolute, rather than on a per body weight basis will eliminate factors 2 and 4 from the calculation.

Plunger velocity is calculated by dividing the infusion flow by:

6. The inverse of the plunger cross section of the syringe 11.

When operating in the "Infusing" mode, only the plunger velocity needs to be calculated. However, when operating in the "Bolusing" mode, the following values need to be calculated. The microprocessor 66 calculates the desired pumping time as a product of the factors below:

7. The bolus as indicated by the position of the bolus knob 18.
8. The inverse of the infusion rate indicated by the position of infusion rate knob 14. This is the inverse of Factor 1.
9. A scaling factor to convert the position of the bolus knob 18 to the bolus indicated on scale 44 of the magnetic label 30.
10. A scaling factor to convert the inverse of the infusion rate indicated by the position of infusion rate knob 14 to the inverse of the infusion rate indicated on scale 40 of the magnetic label 30.

Total Bolus Volume is calculated by multiplying Infusion Flow by Bolus Duration.

Those skilled in the art will realize that these calculations may be done in different orders and that other factors may be necessary for some applications.

The microprocessor 66 receives factors 1, 2, and 7 from parallel to serial converter which in turn receives these values from the twelve position rotary switches 68, 70 and 72 associated with knobs 14, 16 and 18. The microprocessor 66 does the necessary inverse calculations, including that to derive factor 8 from factor 1. The microprocessor 66 uses the data from the Hall Effect sensors to assemble a digital word to index into the non-volatile memory of microprocessor 66, such as read-only-memory (ROM), to retrieve factors 3-5, 9, and 10 listed above. As will be described later in more detail, there are some infusion modes where the bolus or body weight scales are replaced by extended range infusion rate scales. In those modes, knob positions are interpreted differently in accordance with their changed function as indicated by the configuration of magnets 50, 51 in label 30. Those skilled in the art will easily recognize the change in interpretation of the knobs. Those skilled in the art will realize that several of these factors could be stored as factors pre-multiplied together with each other. Those skilled in the art will also realize that since products of various factors are retrieved from the non-volatile memory of microprocessor 66, that a single product is applicable to many individual configurations of the various factors.

Factor 6 is obtained by using the position of syringe type switch 21 feeding into microprocessor 66.

The microprocessor 66 then communicates the values of plunger velocity, infusion flow, total bolus volume and bolus duration to the drive mechanism 74 of the syringe 11. Further, microprocessor 66, using the position of knobs 14, 16, 18, 20, and feedback information from the drive mechanism 74 of the syringe 11 to operate light emitting diodes 22, 24, 26, liquid crystal display 28, and audible alarm 29.

Drive mechanism 74 includes motor 76, motor pulse width modulated driver 78, motor brake 80, primary encoder 82 and secondary encoder 84. Motor pulse width modulated driver 78 is responsive to pulses from microprocessor 66. Motor 76 is responsive to motor pulse width modulated driver 78. Motor 76 drives the plunger driver 23 which, in turn, drives syringe 11. Motor speed is corrected as the microprocessor 66 reads the primary encoder 82 and adjusts the pulse width modulated speed control algorithm within microprocessor 66 for the proper speed. The secondary encoder 84 monitors the rotation of the leadscrew (not shown) of motor 76 and is used for safety purposes, such as primary encoder failure. Motor brake 80 is used to decrease coasting of the motor 80 and to prevent backward motion thereof.

FIG. 5 shows a detailed exploded view of apparatus 10. Magnetic label 30 includes a front sheet 84 glued over a flexible magnetic sheet 86, into which strong magnets 50, 51 are placed. Rear sheet 88 is glued over the rear of the label 30. Knobs 14, 16, 18 and 20 are inserted into front plate 12 which is backed by steel foil 90 and plastic cover 92. A Hall Effect PC board 94 with Hall Effect Sensors 54–59 is sandwiched between plastic cover 92 and switch PC board 96 which contains most of the electronics including microprocessor 66. All of this fits into pump body 98.

To use this apparatus 10, a user is supplied a syringe 11 and a magnetic label 30 from a pharmaceutical manufacturer. Magnets have been placed into apertures 46, 48, and 50 of the magnetic label 30 in a configuration which will ensure proper calculation of the pumping time and rate. The user places the syringe 11 into the drive mechanism 70 and the magnetic label 30 onto the apparatus. As previously stated, exactly two magnets must be in the label 30 and the label 30 must be placed onto the apparatus 10 for the apparatus 10 to operate. The user sets the operational mode selection knob 20 to the "Stop/Confirm" position. LCD 28 will then display a label identification code. The user verifies that this matches the label identification code on the alphanumeric listing 32 of label 30. The user fills a 20 or 60 cc (cubic centimeter) syringe 11 with the amount of pharmaceutical product required. The user confirms that the concentration of the pharmaceutical product or infusate matches the concentration listed on the alphanumeric listing 32 of label 30. The user attaches tubing (not shown) to the syringe 11, and attaches the syringe 11 to clip 13 and to plunger driver 23. The user uses prior art practices to attach a flow set (not shown) to the syringe 11 and to remove air from the line, etc. The user turns the operational mode selection knob 20 to the "purge" position until fluid flow occurs. The "purge" position should not be used while the apparatus 10 is connected to the patient. The flow set (not shown) is attached to the patient's primary I.V. line (not shown).

The user then, depending upon the functions and values encoded into the label 30, enters into one of three modes:

1. Delivery of an infusion based on an infusion rate given by body weight with the capability of giving a loading dose or supplemental bolus dose.

The user sets the patient weight knob 20 and the infusion rate knob 14 and sets the operational mode selection knob 20 to "Infuse". The microprocessor 66 will choose a plunger velocity but will not limit the infusion to a given time or volume. The "Infusing" LED 22 will go on, the LCD 28 will incrementally display the amount of pharmaceutical product delivered. The infusion will stop when the user turns the infusion rate knob 14 to "0", when the user turns the operation mode selection knob 20 to Stop/Confirm, or when the syringe 11 is empty.

To administer a loading dose or supplemental bolus, the user set the desired dose on the Bolus knob 18, and rotates the operational mode selection knob 20 to "Bolus Start". The user releases the knob 20, which is spring loaded in this position, when a short audible beep is generated by audio driver 67. The "Bolusing" Light Emitting Diode 26 will flash as an indicator of normal bolus delivery. The Liquid Crystal Display 28 will count upward (on a per kilogram of patient body weight basis) to show the status of the present bolus. To terminate a bolus, the user rotates the operational mode selection knob 20 to "Stop/Confirm". Once a bolus is initiated, changes to the patient weight knob 16 or bolus knob 18 will not affect the bolus.

2. The delivery of infusion based on high and low rates independent of body weight.

In this mode, the Infusion Rate Scale 40 and Body Weight Scale 42 are replaced by a High Infusion Rate and a Low Infusion Rate Scale, respectively. The user sets one of these knobs to zero, and the other knob to the desired value, depending upon whether a high or low infusion rate is desired. The user then turns the operational mode selection knob 20 to "Infuse". The "Infusing" Light Emitting Diode 22 will flash and the Liquid Crystal Display 28 will begin incrementing to indicate the amount of pharmaceutical product delivered. To change the rate, the user rotates either infusion rate knob to a new position. To stop an infusion, the user either sets both infusion rate knobs to zero, or turns the operational mode selection knob 20 to "Stop/Confirm".

3. The delivery of an infusion based on high and low infusion rates given by weight.

In this mode, the Infusion Rate Scale 40 and Bolus Scale 42 are replaced by a High Infusion Rate and a Low Infusion Rate Scale, respectively. The user sets one of these knobs to zero, and the other knob to the desired value, depending upon whether a high or low infusion rate is desired. The user sets the patient weight on patient weight knob 14. The user then turns the operational mode selection knob 20 to "Infuse". The "Infusing" Light Emitting Diode 22 will flash and the Liquid Crystal Display 28 will begin incrementing to indicate the amount of pharmaceutical product delivered. To change the rate, the user rotates either infusion rate knob to a new position. To stop an infusion, the user either sets both infusion rate knobs to zero, or turns the operational mode selection knob 20 to "Stop/Confirm".

The apparatus 10 has the following warning indicators:

1. End of Syringe or Occlusion—This is indicated by a pulsating audible alarm from audio driver 67 and flashing "Attention" Light Emitting Diode 24. Liquid Crystal Display 28 will indicate which condition exists.
2. Low Battery—This is indicated by a flashing "Attention" Light Emitting Diode 24 without activating audio driver 67. Liquid Crystal Display 28 will indicate this condition.
3. Internal Fault—This is indicated by an audible alarm from audio driver 67 and all light emitting diodes 22, 24 and 26 coming on simultaneously.
4. Improper Switch Position—If any switch or knob is left in or held in a position between actual selections for over one-half second, the apparatus 10 will alarm with three short audible beeps from audio driver 67. The apparatus 10 will continue to infuse at the previously chosen rate. Repositioning the switch to the proper location will terminate the alarm.

Thus the several aforementioned objects and advantages are most effectively attained. Although a single preferred embodiment of the invention has been disclosed and described in detail herein, it should be understood that this invention is in no sense limited thereby and its scope is to be determined by that of the appended claims.

What is claimed is:

1. An apparatus comprising:
   pumping means;
   means for controlling operation of said pumping means, including sensing means and manual controls for manually setting the desired operation of said pumping means; and
   indicator means, separable from said means for controlling, which includes:
      information in a pre-arranged configuration for a selected mode of pump operation; and
      visual scales corresponding to said pre-arranged configuration, said visual scales indicating the desired setting for said manual controls when said indicator means is placed adjacent to said manual controls;
   wherein said sensing means senses said pre-arranged configuration and is responsive thereto to alter calculations for controlling said pumping means in accordance with said pre-arranged configuration and with said visual scales when said indicator means is placed adjacent to said manual controls.

2. The apparatus of claim 1 wherein said information is encoded by positioning of magnets.
3. The apparatus of claim 1 wherein the apparatus is a medical pump and wherein said pumping means includes means for engaging a syringe.
4. The apparatus of claim 1 wherein said manual controls include a patient weight control knob.
5. An apparatus comprising:
   pumping means;
   means for controlling operation of said pumping means, including manual controls; and
   indicator means which includes information in a pre-arranged configuration of magnets for a selected mode of pump operation, wherein said means for controlling senses said pre-arranged configuration when said indicator means is placed adjacent to said means for controlling and wherein said means for controlling controls said pumping means in accordance with said pre-arranged configuration;
   wherein said indicator means further includes visual scales for said manual controls when said indicator means is placed adjacent to said means for controlling, wherein said visual scales are in accordance with said pre-determined configuration and wherein said means for controlling uses said pre-arranged configuration to alter the calculations in accordance with said visual scales; and
   wherein said indicator means is held in position adjacent to said means for controlling by magnetic means.
6. The apparatus of claim 5 wherein said means for controlling further includes Hall Effect sensors which sense said pre-arranged configuration of said magnets.
7. The apparatus of claim 6 wherein said Hall Effect sensors sense the polarity of said magnets in said pre-arranged configuration.
8. The apparatus of claim 7 wherein said pumping means drives a medical syringe.
9. The apparatus of claim 8 wherein said means for controlling includes a microprocessor.
10. The apparatus of claim 8 wherein said means for controlling allows said pumping means to operate only if a predetermined number of said magnets are in said pre-determined configuration.
11. The apparatus of claim 8 wherein said pumping means can run at a constant flow rate.
12. The apparatus of claim 8 wherein said pumping means can run at a constant flow rate for a given period.
13. The apparatus of claim 12 wherein said manual controls include a patient weight control knob, wherein said given period is determined from a setting of said patient weight control knob.
14. The apparatus of claim 8 further including lights for indicating said selected mode of operation.
15. The apparatus of claim 8 further including a multi-character display for indicating total flow amount from said pumping means.
16. The apparatus of claim 5 wherein the apparatus is a medical pump and wherein said pumping means includes means for engaging a syringe.

* * * * *